United States Patent [19]
Cho et al.

[11] Patent Number: 5,529,769
[45] Date of Patent: Jun. 25, 1996

[54] COSMETIC COMPOSITIONS CONTAINING BETULINIC ACID

[75] Inventors: Suk H. Cho, Bogota; Keith Gottlieb, Fort Lee; Uma Santhanam, Tenafly, all of N.J.

[73] Assignee: Chesebrough-Pond's USA Co., Division of Conopco, Inc., Greenwich, Conn.

[21] Appl. No.: 359,976

[22] Filed: Dec. 20, 1994

[51] Int. Cl.$^6$ .............................. A61K 7/06; A61K 35/78
[52] U.S. Cl. .......................... 424/74; 424/61; 424/195.1; 514/846; 514/847; 514/860
[58] Field of Search .................................. 424/61, 195.1, 424/74, 484; 514/860, 846, 847

[56] References Cited

U.S. PATENT DOCUMENTS

5,051,449  9/1991  Kligman ................................. 514/559

FOREIGN PATENT DOCUMENTS

63-198888  8/1988  Japan .
04217861   8/1992  Japan .
0578870    3/1993  Japan .

OTHER PUBLICATIONS

*The Merck Index*, pp. 185–186 (1989).

Kligman, A., "Early Destructive Effect of Sunlight on Human Skin", *JAMA* (Dec. 29, 1969), vol. 210, pp. 2377–2380.

Lavker, R., "Structural Alteration in Exposed and Unexposed Aged Skin", *Journal of Investigative Dermatology*, (1979), vol. 73, pp. 59–66.

Smith, J. et al., "Alterations in Human Dermal Connective Tissue with Age and Chronic Sun Damage", *Journal of Investigative Dermatology*, (1962), vol. 39, pp. 347–350.

Shuster, S. et al., "The Influence of Age and Sex on Skin Thickness, Skin Collagen and Density", *British Journal of Dermatology* (1975), vol. 93, pp. 639–643.

Chen, S. et al., "Effects of All-Trans Retinoic Acid on UVB-Irradiated and Non-Irradiated Hairless Mouse Skin", *Society for Investigative Dermatology*, (1992), vol. 98, pp. 248–254.

Griffiths, Christopher, E., et al., "Restoration of Collagen Formation in Photodamaged Human Skin by Tretinoin (Retinoic Acid)", *The New England Journal of Medicine* (1993), vol. 329, pp. 530–535.

Peterkofsky, B., "The Effect of Ascorbic Acid on Collagen Polypeptide Synthesis and Proline Hydroxylation During the Growth of Cultured Fibroblasts", *Archives of Biochemistry and Biophysics*, (1972), vol. 152, pp. 318–328.

Cardinale, G. et al., *Adv. Enzymol.*, (1974), vol. 41, p. 245.

Geesin, J. et al., "Ascorbic Acid Specifically Increases Type I and Type III Procollagen Messenger RNA Levels in Human Skin", *Society for Investigative Dermatology, Inc.*, (1988), vol. 90, pp. 420–424.

Tajima, S. et al., "Regulation of Collagen Synthesis by Ascorbic Acid. Ascorbic Acid Increases Type I Procollagen mRNA", *Biochem. and Biophys. Res. Comm.*, (1982), vol. 106, pp. 632–637.

Vernillo, A. et al., "Stimulation of Collagen and Glycosaminoglycan Production by Phenytoin 5,5–diphenylhydantoin in Monolayer Cultures of Mesenchymal Cells Derived From Embryonic Chick Sternae", *Arch. Oral Biol.*, (1986), vol. 31, pp. 819–823.

Hakeda, Y. et al., "Effect of Forskolin on Collagen Production in Clonal Osteoblastic MC3T3–E1 Cells", *J. Biochem.*, (1987), vol. 101, pp. 1463–1469.

Tenni, R. et al., "Effect of the Triterpenoid Fraction of Centella Asiatica on Macromolecules of the Connective Matrix in Human Skiin Fibroblast Cultures", *J. Biochem*, (1988), vol. 38, pp. 69–77.

Maquart, F. X. et al., "Stimulation de la Synthese de Collagene dans des Cultures de Fibroblastes par des Triterpenes Extraits de Centella Asiatica", *Actualite Therapeutique*, Jun. 8, 1989, pp. 1571–1574.

Lawrence, J. C., "The Morphological and Pharmacological Effects of Asiaticoside upon Skin in vitro and in vivo", *European Journal of Pharmacology*, (1967), pp. 414–425.

Rosen, H. et al., "Effect of Asiaticoside on Wound Healing in the Rat", *J. Proc. Soc. Exp. Biol. Med.*, (1967), vol. 125, pp. 279–280.

Bosse, J. et al., "Clinical Study of a New Antikeloid Agent", *Ann. Plast. Surg.*, (1979), vol. 3, pp. 13–21.

Vogel, H. G. et al., "Effect of Terpenoids Isolated from Centella Asiatica on Granuloma Tissue", *Acta Therapeutica*, (1990), vol. 16, pp. 285–296.

Chopra, R. et al., "Indigenous Drugs of India", Dhur & Sons Pvt. Ltd. (1985), Calcutta, pp. 351–353.

Adolphe, M. et al., "Use of Fibroblast Cell Culture for the Study of Wound Healing Drugs", *International Journal of Cosmetic Science*, (1984), vol. 6, pp. 55–58.

Maquart, F. X. et al., "Stimulation of Collagen Synthesis in Fibroblast Cultures by a Triterpene Extracted From Centella Asiatica", *Connective Tissue Research*, (1990), vol. 24, pp. 107–120.

Abstract of JP 051776688A. (Dec. 1991).

Abstract of JP 57031620A (Jul. 1980).

Nakagawa, et al., "Long-Term Culture of Fibroblasts in Contracted Collagen Gels: Effects on Cell Growth and Biosynthetic Activity", The Society for Investigative Dermatology, Inc., (1989), vol. 93, pp. 792–798.

Jutley, J. K. et al., "Influence of Retinoic Acid and TGF–$\beta$ on Dermal Fibroblast Proliferation and Collagen Production in Monolayer Cultures and Dermal Equivalents", *Matrix*, (1993), vol. 13, pp. 235–241.

Martens et al., "Collagen Synthesis in Fibroblasts from Human Colon: Regulatory Aspects and Differences with Skin Fibroblasts", *Gut*, (1992), vol. 33, pp. 1664–1670.

(List continued on next page.)

*Primary Examiner*—Thurman K. Page
*Assistant Examiner*—Sally Gardner
*Attorney, Agent, or Firm*—Rimma Mitelman

[57] ABSTRACT

Cosmetic compositions containing at least 6 μM of betulinic acid, preferably in combination with ascorbic acid. The compositions are particularly useful in reducing signs of cellulite.

12 Claims, No Drawings

OTHER PUBLICATIONS

Hachem, A. et al., "Histological and Clinical Study of the Effects of Titrated Extract of Centella Asiatica in Localised Lipodystrophy".

Viala, A. et al., "Study of the Transcutaneous Permeation of the Active Ingredients of Titrated Extract of Centella Asiatica L. labelled with Tritium after Application in the Form of A Lano–Paraffin Gauze Dressing and of Ointment", Sep. 29, 1977.

Moloney, Stephen J. et al., "The Hairless Mouse Model of Photaging: Evaluation of the Relationship Between Dermal Elastin, Collagen, Skin Thickness and Wrinkles", *Photochemistry and Photobiology*, vol. 56, No. 4, (1992), pp. 505–511.

COSMETIC COMPOSITIONS CONTAINING BETULINIC ACID

FIELD OF THE INVENTION

The invention relates to compositions for topical application to human skin which compositions contain betulinic acid and to methods of using the compositions for treatment and conditioning of skin.

BACKGROUND OF THE INVENTION

Collagen, the predominant matrix skin protein, is known to impart tensile strength to skin. It has been shown that collagen is significantly reduced with age and UV exposure. The degradation or destruction of the architecture of these proteins decreases the tensile strength of the skin causing wrinkles and laxity. Many studies involving human subjects have shown that collagen type I is decreased with increasing severity of photodamage (See Kligman, A., *JAMA*, (1969), 210, pp. 2377–2380; Lavker, R., *J. Inv. Derm.*, (1979), 73, 79–66; Smith, J. et al., *J. Inv. Derm.*, (1962), 39, pp. 347–350; and Shuster, S. et al., *Br. J. Dermatol.*, (1975), 93, pp. 639–643); and some correlation in the histology of wrinkles and reduction in collagen levels in the sun-exposed skin has been reported. See Chen, S.; Kiss, I., J. Inv. Derm., (1992), 98. pp. 248–254. Voorhees and collegues have supported these findings by showing the restoration of collagen type I in photo-damaged human skin by a topical treatment with tretinoin. See Christopher, E., et al., The New Eng. Jou. of Medicine (1993), 329, pp. 530–535. These results provide the first in vivo evidence that retinoic acid restores collagen type I. Many etiology studies showed a parallel effect between collagen synthesis and wrinkle effacement. It is also believed that the strengthening of the dermal matrix by collagen stimulation may have some beneficial effect for treatment of cellulite. See U.S. Pat. No. 5,051,449 (Kligman).

There are a few natural products which are known to stimulate collagen synthesis. One of these is ascorbic acid, a cofactor for collagen synthesis, known to activate the enzyme prolyl-hydroxylase (See Peterkofsky, B., *Arch. Biochem. Biophys.*, (1972), 152, pp. 318–328) and to increase procollagen mRNA. See Cardinale, G. et al. *Adv. Enzymol.*, (1974), 41, p. 245; Geesin, J. et al., *J. Inv. Derm.*, (1988), 90, p. 420; Tajima, S. et al., *Biochem. Biophys. Res. Comm.*, (1982), 106, pp. 632–637. Stimulation of collagen synthesis by betel nut alkaloids, arecolin and arecaidine, has also been described. See Vermillo, A. et al. *Arch. Oral Biol.*, (1986), 31, pp. 819–823. Forskolin which is a common component of *Coleus forskolli* has been shown to increase the production of collagen in cloned osteoblastic cells. See Hakeda, Y. et al., *J. Biochem.*, (1987), 101, pp. 1463–1469. Excluding ascorbic acid, these agents are not acceptable for cosmetic or personal care use due to their potential toxicity.

Some studies indicate that *Centella asiatica* promotes greater elasticity and suppleness to the skin by its action on the collagen synthesis by the fibroblasts. See Tenni, R. et al., *J. Biochem*, (1988), 38. pp. 69–77; Maquart, F. et al., *Actualite Therapeutique*, (1989), pp. 1571–1574. *Centella asiatica* also acts as a regulating agent in the connective tissue, promoting its regeneration and preventing its excessive proliferation, producing supple, healthy connective tissue. See Lawrence J. *Eur. J. Pharmacol.*, (1967), pp. 414–425; Rosen, H. et al., *J. Proc. Soc. Exp. Biol. Med.*, (1967), 125, pp. 279–280; Bosse, J. et al.; *Ann. Plast. Surg.*, (1979), 3, pp. 13–21. Vogel et al. have shown a significant increase of collagen in scar tissue leading to an increased resistance to traction and rupture. See Vogel, H. et al., *Acta Therapeutica*, (1990) 16, pp. 285–296. This increased resistance of the collagen fibers is only noticeable in collagen which has reached a certain maturation stage. The triterpenes of *Centella asiatica* increase both the collagen synthesis and its maturation level.

The plant, *Centella asiatica*, grows in Madagascar and around the Indian Ocean. Traditionally, this plant has been used for wound healing. See Chopra, R. et al., "Indigenous Drugs of India", Dhur & Sons Pvt. Ltd. (1985), Calcutta. In Europe, a drug prepared from this plant is used for the treatment of ulcers and wounds. *Centella asiatica* is also suitable for cosmetic use, i.e., skin conditioning improvement, anti-cellulite effect, and improvements in skin color. See Adolphe, M. et al., *Int. J. Cosmetic Soc.*, (1984), 6, pp. 55–58. *Centella asiatica* contains asiatic acid, madecassic acid, asiaticoside and madecaside, all of which belong to the class of triterpenoids. Maquart et al., *Conn. Tissue Res.*, (1990), 24 pp. 107–120 showed that the triterpene extract from *Centella asiatica* stimulated collagen synthesis in fibroblast monolayer cultures, and asiatic acid was found to be the major component responsible for collagen synthesis stimulation.

The present invention is based at least in part on the discovery that betulinic acid has better collagen stimulation activity than *Centella asiatica* extract or active components of *Centella asiatica*. Unlike the structural configuration of triterpenes like asiatic acid or asiaticoside, betulinic acid has a fused five member ring and contains exo-vinyl group as illustrated in Figure below. The use of betulinic acid and plants containing betulinic acid in foods and flavors has been disclosed. See JP 051776688A; JP 57031620A.

It is an object of the present invention to provide cosmetic compositions containing an active component which is safe, yet is more effective than *Centella asiatica* or the active components of *Centella asiatica*.

It is another object of the present invention to provide cosmetic compositions containing betulinic acid.

It is yet another object of the invention to provide a method of treating skin and of stimulating collagen synthesis in skin.

These and other objects of the invention will become more apparent from the detailed description and examples that follow.

SUMMARY OF THE INVENTION

The above objects are attained by the present invention which includes, in part, a novel composition containing a pharmaceutically or cosmetically acceptable carrier and at least 6 μM of betulinic acid. The present invention is based at least in part on the discovery that betulinic acid stimulates collagen synthesis to a greater degree than *Centella asiatica* extract or active components of *Centella asiatica*.

In the preferred embodiment of the invention the compositions further comprise ascorbic acid which may be present as an acid or in the form of an ester or a salt. It has been found as part of the present invention that the presence of ascorbic acid is necessary in order for betulinic acid to stimulate collagen synthesis. However, sufficient amount of ascorbic acid is present in human skin tissue to act in conjunction with exogenously applied betulinic acid to stimulate collagen synthesis. Nevertheless, the inclusion of additional ascorbic acid into inventive compositions is particularly beneficial.

The invention also includes methods of treating skin by applying topically thereto the inventive compositions containing betulinic acid. The invention also includes a method of stimulating collagen synthesis by applying thereto the inventive compositions. Compositions are useful in preventing or repairing such skin conditions as wrinkling, laxity, cellulite, and photodamage, in order to attain smooth, and supple skin with high elasticity.

DETAILED DESCRIPTION OF THE INVENTION

Betulinic acid is the essential ingredient of the inventive compositions. Betulinic acid has the following formula:

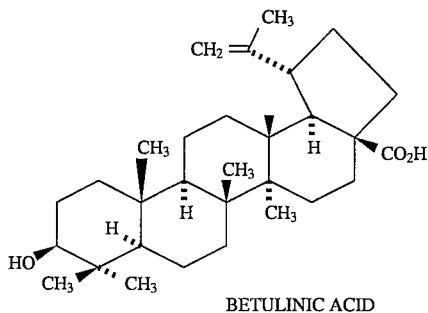

BETULINIC ACID

According to the present invention, betulinic acid must be present in the composition in an amount of at least 6 µM. Preferably, the concentration of betulinic acid in the inventive compositions is in the range of from 61 µM to 100 mM, most preferably in the range of from 6 µM to 50 mM to attain optimum collagen stimulating activity at a minimum cost.

Betulinic acid may be obtained commercially as pure betulinic acid, 90% pure beutlinic acid from Aldrich, or as a plant extract.

According to the ["Handbook of Phytochemical Constituents of GRAS (also known as generally recognized as safe) herbs and Other economic plants" By James Duke 1992, CRC Press], following plants are shown to contain betulinic acid.

*Broussonetia papyrifera*
*Arctostaphylos uva-ursi*
*Eucalyptus citriodora*
*Carya ovata*
*Viscum alkeem*
*Vitis vinifera*
*Menyanthes trifoliata*
*Jugalns negia*
*Lantana camara*
Betula spp. (e.g., silver birch)

The plant extracts containing betulinic acid suitable for use in present compositions are organic solvent extracts, e.g., alcoholic extracts, ethyl acetate extracts, propylene glycol extracts, ethylene glycol extracts, ether extracts. It should be understood that when a plant extract is used as a source of betulinic acid, the plant extract must be present in a sufficient amount to provide at least 6 µM concentration of betulinic acid in the composition. According to Duke, the concentration of betulinic acid in plants varies from 1 ppm to 8000 ppm by weight. The concentration is also affected by other variables (such as plant parts, climate, location, soil condition, and way one process the extract).

The composition according to the invention also comprises a cosmetically acceptable vehicle to act as a dilutant, dispersant or carrier for the active components in the composition, so as to facilitate their distribution when the composition is applied to the skin, hair and/or nails.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

The cosmetically acceptable vehicle will usually form from 5 to 99.9%, preferably from 25 to 80% by weight of the emulsion, and can, in the absence of other cosmetic adjuncts, form the balance of the composition.

A preferred optional ingredient present in the inventive compositions is ascorbic acid. Although the co-presence of ascorbic acid is necessary to attain the collagen synthesis stimulating activity, sufficient ascorbic acid is present in human skin to act as a co-active for betulinic acid. However, the inclusion of ascorbic acid in the inventive compositions is preferred in order to attain optimum collagen synthesis stimulating activity. Ascorbic acid may be present as salt (e.g., sodium ascorbate, calcium ascorbate) or ester (ascorbyl palmitate, ascorbyl acetate), or acid. The range of ascorbic acid in the present compositions is from 0.01% to 15%, preferably 0.05% to 10%, most preferably 0.1% to 5%. The preferred agent is ascorbyl palmitate in order to improve the uniformity and stability of the formulation.

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Actives are defined as skin or hair benefit agents other than emollients and other than ingredients that merely improve the physical characteristics of the composition. Although not limited to this category, general examples include lipolytic agents and vasodilating agents, sunscreens and tanning agents.

Due to collagen synthesis stimulating activity of inventive compositions, the inclusion of lipolytic and vasodilating agents into the inventive compositions is particularly preferred in order to attain maximum anti-cellulite benefits.

Suitable lipolytic agents include but are not limited to caffeine, theophylline, epinephrine, isoproterenol, forskolin, yohimbine, and other agents such as those acting as phosphodiesterase inhibitors, or β-agonists or α-2-adrenergic antagonists, cAMP analogs or adenylate cyclase activators.

Suitable vasodilating agents include but are not limited to escin, ginkgo biloba, ivy, minoxidil, nicotinates, methyl salicylate, or other agents acting as α-adrenergic antagonists, β-adrenergic agonists, or releasor of nitrooxides.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Surfactants, which are also sometimes designated as emulsifiers, may be incorporated into the cosmetic compositions of the present invention. Surfactants can comprise anywhere from about 0.5% to about 30%, preferably from about 1% to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and/or dialkyl phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust bean gum. Under certain circumstances the thickening function may be accomplished by a material also serving as a silicone or emollient. For instance, silicone gums in excess of 10 centistokes and esters such as glycerol stearate have dual functionality.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

The composition according to the invention is intended primarily as a product for topical application to human skin, especially as an agent for improving the condition of photodamaged skin, aged skin, or reducing cellulitis, improving firmness and elasticity, reducing the permeability to water of the skin, in order to generally to enhance the quality and flexibility of skin. The composition can also be applied to hair and nails.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

The inventive compositions can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. When compositions according to the invention include ascorbic acid, dual compartment packaging is preferred to further stabilize ascorbic acid so that ascorbic acid may be separated during storage from the rest of the composition.

The invention accordingly also provides a closed container, preferably a dual compartment container, containing a cosmetically acceptable composition as herein defined.

The following specific examples further illustrate the invention, but the invention is not limited thereto.

EXAMPLES

Materials and Methods

Cell Cultures

The protocol outlined by Nakagawa, et. al., *J. Inv. Derm.*, (1989), 93, pp. 792–798, and Jutley, J. K. et al., *Matrix*, (1993) 13, pp. 235–41 was followed quite closely with a few minor modifications. The culture media were from GIBCO, and the plastic culture dishes (non-treated 96 well plates) were from Costar. Human dermal fibroblasts (Clonetics or ATCC) were cultured in a Minimum Essential Medium (MEM)+10% Fetal Bovine Serum (FBS). Typically, the experiments were performed on the sixth to ninth passages. Dermal equivalents were prepared using Vitrogen 100 (purified, pepsin-solubilized bovine dermal collagen) from Celtrix Corp. The fibroblasts were mixed with neutralized collagen to give a final concentration of $2.5 \times 10^5$ cells/mL and 1.5 mg collagen per mL of gel. The mixture was then seeded in non-treated 96-well plates in aliquots of 100 μL/well. The gels were allowed to polymerize for 60 minutes at 37° C., then the MEM+10%FBS was added to each well in 100 μL aliquot. The sterility of the cultures was checked regularly, and cell counts were performed using routine techniques.

Incubations

Cells were incubated at 37° C. for 24 hours in a 5% $CO_2$ and 95% air atmosphere. After 24 hours, the cultures were given fresh FBS-free MEM and 50 μg/mL ascorbic acid and an extract or active. The test dishes were supplemented with various concentration of actives. Transforming growth factor-B 1 (TGF-β) at 10 ng/mL was used as the positive control for the collagen assay. After an additional day of incubation, the cultures were given either 20 μCi/mL of [2,3-$^3$H] or 2 μCi/mL of $^{14}$C proline and fresh ascorbic acid at 50 μg/mL. The test plates were then further incubated for 24 hours.

Measuring Collagen and Protein Synthesis

At the end of the incubation period, the gels were dissolved using 100 μL of 50 mM HCl and heated at 37° C. for 60 minutes or until the gel was completely dissolved. After neutralization with NaOH, the samples were transferred from the original culture plates to round bottom, high protein binding Elisa 96-well plates (Corning). The samples were split, and a buffer A containing Tris-HCl (120 mM, at pH 7.2) and calcium acetate (24 mM) was added to each well, bringing the total volume up to 150 μL. The other half of the samples were treated with bacterial collagenase (Worthington) and buffer A, and both sets of samples were left at 37° C. for 18–24 hours. Bovine serum albumin (BSA) (3 mg/mL) was added to the samples to act as a carrier protein. Then the samples were precipitated at 4° C. for 30 minutes in the presence of 10% trichloroacetic acid (TCA) and centrifuged at 2750 RPMs for 10 minutes. Two washes in 5% TCA were performed, and the final pellets were dissolved in 100 μL of 0.1 M NaOH for 60 minutes at 50° C. The 100 μL samples were added to 5 mL of scintiverse and counted on a Beckman scintillator. The percentage of new collagen synthesis was calculated using the formula similar to that described by Martens et al., Gut, (1992), 33, pp. 1664–1670. The equation is as follows:

$$\% \text{ collagen} = 100\% \times (b-c)/[c \times 5.4 + (b-c)]$$

where b=total proline incorporated; C=proline incorporated in non-collageneous proteins The data was then further equated for relative comparison with TGF-β, and the equation is as follows:
Total Collagen increase=avg. total proline incorporation (active)×relative % collagen increase calculated from above equation/avg. total proline (control)×relative % collagen increase from above equation.

EXAMPLE 1

The stimulating activity on collagen synthesis by a fibroblast culture treated with triterpenes from the plant *Centella asiatica*, and *Centella Asiatica* was investigated. *Centella asiatica* was purchased from Sigma; asiatic acid and asiaticoside were obtained from MMP (Mountainside, N.J.). Asiatic acid, asiaticoside, and *Centella asiatica* tincture at various concentrations were tested in a dermal equivalent assay. In order to normalize the results, each experiment was compared to the control. The results that were obtained are summarized in Table 1.

TABLE 1

The Effect on Collagen Synthesis of *Centella asiatica* and Active Components of *Centella asiatica*

| Experiment Number: | Total Protein (DPM ± SE) | Non Collagen Protein (DPM ± SE | Percent Collagen Synthesis | Percent increase compare to Control |
|---|---|---|---|---|
| Exp 1: Control | 25055 ± 1832 | 18641 ± 871 | 5.85 ± 0.7 | — |
| *Centella asiatica* @ 10 mg/mL | 28716 ± 1684 | 20793 ± 693 | 6.46 ± 0.72 | ≅130% |
| *Centella asiatica* @ 25 mg/mL | 23295 ± 721 | 14719 ± 1260 | 11.09* ± 2.41 | ≅175% |
| Exp 2: Control | 36131 ± 2866 | 29442 ± 3206 | 4.59 ± 1.11 | — |
| Asiaticoside @ 5 μM | 37640 ± 1410 | 28972 ± 2238 | 6.17 ± 1.77 | ≅140% |
| Asiaticoside @ 10 μM | 32211 ± 4331 | 17342 ± 1019 | 13.2* ± 3.96 | ≅255% |
| Exp 3: Control | 40088 ± 692 | 34783 ± 721 | 2.78 ± 0.47 | |
| Asiatic acid @ 10 μM | 43255 ± 2381 | 35617 ± 1821 | 3.81* ± 0.14 | ≅150% |
| Asiatic acid @ 20 μM | 38787 ± 1768 | 34055 ± 1671 | 2.52 ± 0.28 | ≅90% |

*$P < 0.05$

The results in Table 1 indicate that asiaticoside and asiatic acid and *Centella asiatica* gave a positive response in stimulation of collagen, but this response was not significant compared to the control.

EXAMPLE 2

Example 1 was repeated except that the effect of betulinic acid on collagen stimulation was investigated. Betulinic acid was purchased from Aldrich and it was 90% pure. Ascorbic acid was purchased from Sigma and it was 99% pure. The results that were obtained are summarized in Table 2.

TABLE 2

The Effect of Betulinic Acid on the Stimulation of Collagen Synthesis

| Experiment Number: | Total Protein (DPM ± SE) | Non Collagen Protein (DPM ± SE | Percent Collagen Synthesis | Percent increase compare to Control |
|---|---|---|---|---|
| Exp 1: Control | 10719 ± 1243 | 9030 ± 1314 | 3.88 ± 1.45 | |
| Betulinic acid @ 23 μM | 24416 ± 1285 | 11913 ± 249 | 16.22* ± 0.92 | ≅690% |
| Betulinic acid @ 61 μM | 18605 ± 1113 | 14227 ± 1139 | 5.79* ± 2.18 | ≅260% |
| Exp 2: Control | 53958 ± 4658 | 51627 ± 3231 | 0.8 ± 0.45 | |
| Betulinic acid @ 23 μM | 50190 ± 805 | 40582 ± 920 | 4.26 ± 0.58 | ≅490% |

*$P < 0.05$

The results in Table 2 indicate that the level of stimulation by betulinic acid is substantially higher than stimulation observed in Example 1 when *Centella asiatica* or its components were employed. We observed nearly 5 to 6 fold increase in collagen synthesis. Clearly the structural differences between betulinic acid and other triterpenes (e.g., those found in *Centella asiatica*) have triggered a greater response in collagen synthesis.

EXAMPLE 3

Table 3 shows the dose response study of betulinic acid on collagen synthesis stimulation.

TABLE 3

Dose Response Study on Betulinic acid with Carbon-14 Preline

| Concentration (μM) | Fold Increase |
|---|---|
| 5.6 | 0.8 |
| 11.0 | 1.4* |
| 22.0 | 1.8* |
| 44.0 | 2.6* |

*$p < 0.05$

The results in Table 3 indicate that betulinic acid starts to stimulate collagen synthesis at a concentration of about 6 μM.

EXAMPLE 4

This example investigates the effect on collagen synthesis of crude plant extracts. Eucalyptus, ginseng, calendula and silver birch extracts were investigated. Eucalyptus was obtained from Botanicals International (Long Beach, Calif.); Ginseng from Weinstein Nutritional Products (Costa Mesa, Calif.), Calendula from MMP, silver birch from Ichimura (Japan). Silver birch and eucalyptus are known to contain betulinic acid, but not the other extracts investigated here. Only the silver birch extract showed a slight positive response. The results that were obtained with silver birch extract are summarized in Table 4.

TABLE 4

The Effect of plant extracts on the Stimulation of Collagen Synthesis

| Experiment Number: | Total Protein (DPM ± SE) | Non Collagen Protein (DPM ± (SE | Percent Collagen Synthesis | Percent Control |
|---|---|---|---|---|
| Exp 1: Control | 59233 ± 1243 | 51603 ± 2882 | 2.92 | |
| Silver Birch @ 10 mg/ml | 58986 ± 1747 | 39514 ± 1244 | 4.43 | ≅151% |
| Silver Birch @ 25 mg/ml | 59515 ± 1994 | 49487 ± 2440 | 3.65 | ≅125% |

*$P < 0.05$

The response was minimal compared to pure betulinic acid (see Examples 2 and 3), and this is probably due to the very low concentration of betulinic acid in the crude extract.

EXAMPLE 5

The effect of other triterpenes on collagen synthesis was investigated. Friedelin and oleanolic acid were purchased from Aldrich. The results that were obtained are summarized in Table 5.

TABLE 5

The Effect of other triterpenes on collagen stimulation

| Experiment Number: | Total Protein (DPM ± SE) | Non Collagen Protein (DPM ± (SE | Percent Collagen Synthesis | Percent increase compare to Control |
|---|---|---|---|---|
| Control | 10719 ± 1243 | 9030 ± 1314 | 3.88 | — |
| Friedelin @ 23 μM | 24042 ± 1264 | 18250 ± 2198 | 6.1 | ≅340% |
| Friedelin @ 59 μM | 14775 ± 703 | 11667 ± 1360 | 5.58 | ≅175% |
| Oleanolic acid @ 55 mM | 17960 ± 3672 | 13958 ± 3273 | 5.62 | ≅240% |

*$P < 0.05$

The results in Table 5 indicate that not all triterpenes stimulate collagen synthesis. Although friedelin and oleanolic acid had some response, it was not significantly different from asiatic acid or asiaticoside (see Example 1). The significant effect of betulinic acid was not seen with crude extracts or pure triterpenes.

EXAMPLE 6

The effect of betulinic acid on collagen synthesis in the absence of ascorbic acid was investigated. The results that were obtained are summarized in Table 6.

TABLE 6

| Compound | Total Protein (DPM ± SE) | Non Collagen Protein (DPM ± (SE | Percent Collagen Synthesis | Percent Control |
|---|---|---|---|---|
| Control w/ Ascorbic acid (50 μg/mL) | 36131 ± 2866 | 29422 ± 320 | 4.59 | |
| Control w/o Ascorbic acid | 2046 ± 112 | 1529 ± 129 | 5.96 ± 1.66 | |
| Betulinic 0.55 μM | 2254 ± 115 | 1731 ± 127 | 5.37 ± 2.18 | ≅99% |
| Betulinic 11 μM | 2144 ± 123 | 1689 ± 173 | 4.87 ± 2.16 | ≅85% |
| Betulinic 55 μM | 2174 ± 122 | 1666 ± 164 | 5.43 ± 1.69 | ≅97% |
| Silver Birch (50 μg/mL) | 2248 ± 234 | 1660 ± 178 | 6.20 ± 1.88 | ≅114 |

The results in Table 6 indicate that betulinic acid and silver birch extract had no significant effect on collagen synthesis and other protein synthesis in the absence of ascorbic acid. However, once applied to skin betulinic acid present in the inventive compositions acts in conjunction with ascorbic acid which is present in human skin. In an adult with minimal concentration of vitamin C, the concentration in plasma reaches about 45 μM of ascorbic acid. Therefore, betulinic acid will still be able to stimulate collagen synthesis even when ascorbic acid is not present in compositions.

EXAMPLE 7

A typical cosmetic composition according to the invention is as follows:

|  | % w/w |
| --- | --- |
| Betulinic acid | 0.5 |
| Fully hydrogenated coconut oil | 3.9 |
| Ceramide | 3 |
| Brij 92* | 5 |
| Bentone 38 | 0.5 |
| Preservative | 0.3 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 8

This example illustrates an oil-in-water cream according to the invention.

|  | % w/w |
| --- | --- |
| Ascorbic acid | 1.0 |
| Betulinic acid | 0.3 |
| Mineral oil | 4 |
| Thiolactate | 2 |
| Brij 56* | 4 |
| Alfol 16RD** | 4 |
| Triethanolamine | 0.75 |
| Butane-1,3-diol | 3 |
| Xanthan Gum | 0.3 |
| Preservative | 0.4 |
| Perfume | qs |
| Butylated hydroxy toluene | 0.01 |
| Water | to 100 |

*Brij 56 is cetyl alcohol POE (10)
**Alfol 16RD is cetyl alcohol

EXAMPLES 9 and 10

The following compositions according to the invention represent lotions which can be used in the treatment of dry skin:

|  | % w/w | |
| --- | --- | --- |
|  | 9 | 10 |
| Ascorbic palmitate | 6.0 | 4.0 |
| Betulinic acid | 0.3 | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilized Demineralized Water | to 100 | to 100 |

EXAMPLE 11

An alcoholic slimming (anti-cellulite) gel according to the invention is as follows:

| Carbopol 940 | 0.8% |
| --- | --- |
| Ethyl alcohol | 25.0% |
| Betulinic acid | 0.5% |
| Triethanolamine | 0.3% |
| Perfume | 0.1% |
| Preservative | 0.1% |
| Ivy extract sold by Indena | 1.0% |
| Escin (sold by Weinstein) | 1.0% |
| Ginko biloba (sold by Weinstein) | 1.0% |
| caffeine | 3.0% |
| Water to | 100% |

EXAMPLE 12

Another slimming (anti-cellulite) gel composition according to the invention is as follows:

| Silicone oil 7158 | 9% |
| --- | --- |
| ceramide | 2.0% |
| squalene | 15.0% |
| petrolatum | 5.0% |
| lanolin | 4.0% |
| Tween 60 | 2.0% |
| cetyl alcohol | 1.2% |
| stearic acid | 2.5% |
| triethanolamine | 0.2% |
| preservative | 0.3% |
| Vitmine E acetate | 0.3% |
| caffeine | 2.0% |
| Escin | 0.5% |
| betulinic acid | 0.5% |
| Ascorbyl palmitate | 0.5% |
| propylene glycol | 5.0% |
| water | 100% |

EXAMPLE 13

Another slimming (anti-cellulite) gel composition according to the invention is as follows:

| Carbopol | 0.8% |
| --- | --- |
| ethoxydiglycol | 4.5% |
| Triethanolamine | 0.5% |
| Caffeine | 2.0% |
| Propyleneglycol | 3.0% |
| Preservative | 0.3% |
| Perfume | 0.4% |
| Silver Birch (betulinic acid) | 2.0% |
| Escin | 1.0% |
| Ginko biloba extract sold by Weinstein | 1.0% |
| Water | 100% |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic composition comprising a cosmetically or pharmaceutically acceptable carrier and betulinic acid in the concentration of at least 6 μM.

2. The composition of claim 1 wherein the concentration of the betulinic acid in the composition is from 6 μM to 100 mM.

3. The composition of claim 1 further comprising an ingredient selected from the group consisting of ascorbic acid, ascorbyl palmitate, sodium ascorbate and mixtures thereof.

4. The composition of claim 3 wherein ascorbic acid is present in an amount of from 0.01% to 15%.

5. The composition of claim 1 wherein the source of betulinic acid is a plant extract.

6. The composition of claim 5 wherein the plant extract is an organic solvent extract.

7. The composition of claim 5 further comprising an ingredient selected from the group consisting of ascorbic acid, ascorbyl palmitate, sodium ascorbate and mixtures thereof.

8. The composition of claim 1 wherein the composition further comprises a lipolytic agent.

9. The composition of claim 8 wherein the lipolytic agent is selected from the group consisting of caffeine, theophylline, epinephrine, isoproterenol, forskolin, yohimbine, phosphodiesterase inhibitors, β-agonists, α-2-adrenergic antagonists, cAMP stimulators, and adenylate cyclase.

10. The composition of claim 9 wherein the composition further comprises a vasodilating agent.

11. The composition of claim 10 wherein the vasodilating agent is selected from the group consisting of ginkgo biloba, ivy, minoxidil, nicotinates, methyl salicylate, adrenergic antagonists, and β-adrenergic agonists.

12. A method of treating skin comprising applying topically thereto the composition of claim 1.

* * * * *